(12) United States Patent
Jung et al.

(10) Patent No.: US 9,329,296 B2
(45) Date of Patent: May 3, 2016

(54) UNDERWATER DETECTOR AND METHOD FOR UNDERWATER DETECTION

(71) Applicant: KOREA INSTITUTE OF GEOSCIENCE AND MINERAL RESOURCES, Daejeon (KR)

(72) Inventors: Hyun-Key Jung, Daejeon (KR); Sung-Ho Cho, Daejeon (KR); Hyo Sun Lee, Daejeon (KR); Hyoung Rae Rim, Daejeon (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 0 days.

(21) Appl. No.: 14/725,814

(22) Filed: May 29, 2015

(65) Prior Publication Data
US 2015/0346373 A1    Dec. 3, 2015

(30) Foreign Application Priority Data
Jun. 2, 2014    (KR) .................. 10-2014-0066744

(51) Int. Cl.
G01R 27/08    (2006.01)
G01V 3/08    (2006.01)
G01N 27/06    (2006.01)

(52) U.S. Cl.
CPC ............... *G01V 3/088* (2013.01); *G01N 27/06* (2013.01)

(58) Field of Classification Search
CPC ............ G01V 3/15; G01V 3/08; G01V 3/081; G01V 3/088; G01V 3/06; G01V 3/20; G01V 3/24; G01V 11/005; G01N 27/06; G01N 27/07; G01N 27/045; G01R 27/22

USPC ............ 324/67, 326, 332, 334, 347, 348, 439, 324/446
See application file for complete search history.

(56) References Cited

U.S. PATENT DOCUMENTS

| 5,517,181 A * | 5/1996 | Gray .................. G01N 27/4162 204/416 |
| 5,598,152 A | 1/1997 | Scarzello et al. |

(Continued)

FOREIGN PATENT DOCUMENTS

| JP | 2007315791 | 12/2007 |
| JP | 2011089799 | 5/2011 |
| KR | 10-1999-0010748 | 10/1999 |

OTHER PUBLICATIONS

James R. Solberg et al. 'Active Electrolocation for Underwater Target Localization.' The International Journal of Robotics Research. May 2008, vol. 27, pp. 529-548.

*Primary Examiner* — Tung X Nguyen
*Assistant Examiner* — Thang Le
(74) *Attorney, Agent, or Firm* — Hauptman Ham, LLP

(57) ABSTRACT

Provided are an underwater detector and a method for an underwater detection, and more particularly, an underwater detector including two direct current electrodes and a plurality of measurement electrodes in order to sense a movement of an object having conductivity different from that of water underwater. Since the underwater detector according to the present invention includes two direct current electrodes, a plurality of measurement electrodes, and a control and measurement module for measuring voltages of the plurality of measurement electrodes, the plurality of measurement electrodes each include an electrode control module and the electrode control module includes a first switch, a second switch, a controlling unit, and the like, the number of voltage measurement lines may be small and a voltage between two selected electrodes may be easily calculated.

5 Claims, 7 Drawing Sheets

(56) References Cited

U.S. PATENT DOCUMENTS

| | | | | |
|---|---|---|---|---|
| 6,404,203 B1 * | 6/2002 | Lagmanson | ............ | G01V 3/02 |
| | | | | 324/347 |
| 9,086,502 B2 * | 7/2015 | Martinez | ............ | G01V 1/20 |
| 2005/0093548 A1 * | 5/2005 | Ueda | ............ | G01V 3/06 |
| | | | | 324/357 |
| 2007/0079653 A1 * | 4/2007 | Zuleta | ............ | G01F 23/26 |
| | | | | 73/304 R |
| 2010/0280773 A1 | 11/2010 | Saether | | |
| 2012/0037512 A1 * | 2/2012 | Robertson | ............ | C02F 1/46109 |
| | | | | 205/759 |

\* cited by examiner (a)        (b)

UNDERWATER DETECTOR AND METHOD FOR UNDERWATER DETECTION

CROSS-REFERENCE TO RELATED APPLICATIONS

This application claims priority under 35 U.S.C. §119 to Korean Patent Application No. 10-2014-0066744, filed on Jun. 2, 2014, in the Korean Intellectual Property Office, the disclosure of which is incorporated herein by reference in its entirety.

TECHNICAL FIELD

The following disclosure relates to an underwater detector and a method for an underwater detection. More particularly, the following disclosure relates to an underwater detector including two direct current electrodes and a plurality of measurement electrodes in order to sense a movement of an object having conductivity different from that of water underwater.

BACKGROUND

Various technologies for detecting an object underwater have been proposed.

One of methods for detecting an underwater object is by using a sound wave, and an underwater object detector using a sound wave has been disclosed in Korean Patent Laid-Open Publication No. 1999-0078351 (publication date: 1999 Oct. 25).

However, in a region in which large noise occurs due to a strong tidal current, or a region in which water layers having temperature and salinity differences are mixed, it is difficult to detect the underwater object using the sound wave.

The other of methods for detecting an underwater object is by using an electromagnetic wave, and a mine detection system using an electromagnetic wave has been disclosed in U.S. Pat. No. 5,598,152 (issue data: 1997 Jan. 28).

However, since the mine detection system disclosed in U.S. Pat. No. 5,598,152 uses a method in which an automatic under vehicle (AUV) sequentially detects a mine while being moved, this method is suitable for detecting a stationary mine, but is unsuitable for detecting a moving object.

SUMMARY

An embodiment of the present invention is directed to providing an underwater detector capable of detecting a moving object even in a region in which large noise occurs due to a strong tidal current, or a region in which water layers having temperature and salinity differences are mixed.

In one general aspect, an underwater detector includes: two direct current electrodes installed underwater and connected to a direct current power supply; a plurality of measurement electrodes installed in a plurality of columns of two or more columns underwater; and a control and measurement module for measuring voltages of the plurality of measurement electrodes, wherein the plurality of measurement electrodes each include an electrode control module, the electrode control module includes a first switch, a second switch, a controlling unit, and a communication unit enabling communication with the control and measurement module, the electrode control module has a first voltage measurement line and a second voltage measurement line which are connected thereto, a connection state between the measurement electrodes and the first voltage measurement line is changed depending on a state of the first switch, a connection state between the measurement electrodes and the second voltage measurement line is changed depending on a state of the second switch, the controlling unit controls the states of the first switch and the second switch, and the voltages of the measurement electrodes are due to an electric field that occurs by a voltage of the direct current electrode.

A direct current voltage may be periodically applied to the two direct current electrodes.

The direct current electrodes and the measurement electrodes may be installed on a sea floor.

In another general aspect, a method for an underwater detection detecting an underwater moving object using an underwater detector including two direct current electrodes installed underwater and connected to a direct current power supply, a plurality of measurement electrodes installed in a plurality of columns of two or more columns underwater, and a control and measurement module for measuring voltages of the plurality of measurement electrodes, includes: applying a direct current voltage to the two direct current electrodes; periodically measuring the voltages of the plurality of measurement electrodes; and estimating the underwater moving object using voltage measurement values, wherein the voltages of the measurement electrodes are due to an electric field that occurs by a voltage of the direct current electrode, the plurality of measurement electrodes each include an electrode control module, and the electrode control module includes a first switch, a second switch, a controlling unit controlling states of the first switch and the second switch, and a communication unit enabling communication with the control and measurement module, such that if two measurement electrodes to be measured are selected when a voltage between the two measurement electrodes is measured, one measurement electrode of the two selected measurement electrodes is connected to the first switch and the other is connected to the second switch to thereby measure the voltage between the two measurement electrodes to be measured.

In another general aspect, a method for an underwater detection detecting an underwater moving object using an underwater detector including two direct current electrodes installed underwater and connected to a direct current power supply, a plurality of measurement electrodes installed in a plurality of columns of two or more columns underwater, and a control and measurement module for measuring voltages of the plurality of measurement electrodes, includes: applying a direct current voltage to the two direct current electrodes; periodically measuring the voltages of the plurality of measurement electrodes; and estimating the underwater moving object using a transition value of voltage measurement values, wherein the voltages of the measurement electrodes are due to an electric field that occurs by a voltage of the direct current electrode, the plurality of measurement electrodes each include an electrode control module, and the electrode control module includes a first switch, a second switch, a controlling unit controlling states of the first switch and the second switch, and a communication unit enabling communication with the control and measurement module, such that if two measurement electrodes to be measured are selected when a voltage between the two measurement electrodes is measured, one measurement electrode of the two selected measurement electrodes is connected to the first switch and the other is connected to the second switch to thereby measure the voltage between the two measurement electrodes to be measured.

DETAILED DESCRIPTION OF EMBODIMENTS

Hereinafter, an underwater detector and a method for an underwater detection according to the present invention will be described in more detail with reference to the accompanying drawings. The drawings of the present invention to be described below are provided by way of example so that the idea of the present invention can be sufficiently transferred to those skilled in the art to which the present invention pertains. Therefore, the present invention is not limited to the drawings provided below but may be modified in many different forms.

Figure 1:
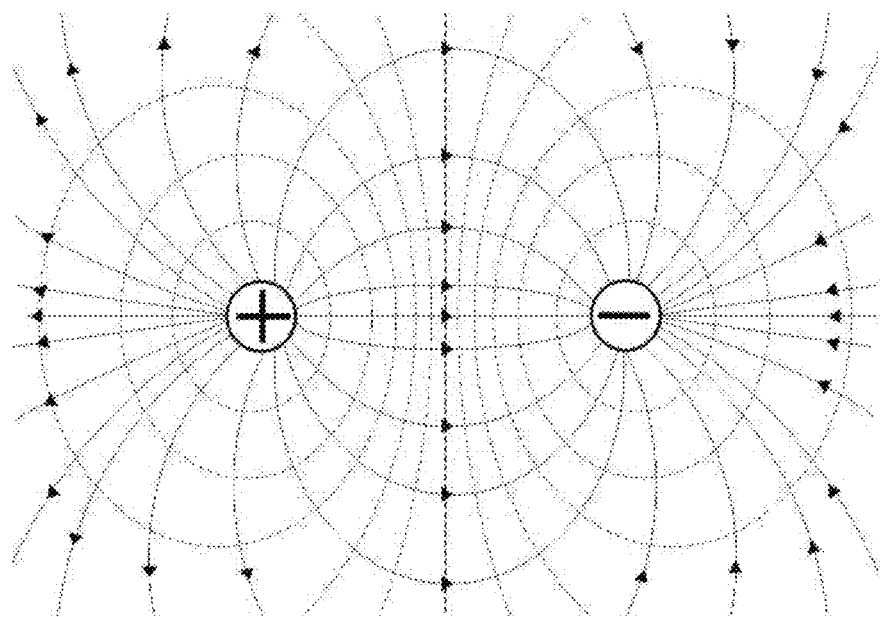
FIG. 1 is a diagram illustrating lines of electric force and equipotential lines when a positive electrode and a negative electrode are present.

FIG. 1 is a diagram illustrating lines of electric force and equipotential lines when a positive electrode and a negative electrode are present. The lines of electric force are indicated by an arrow direction in FIG. 1, wherein a current flows in the direction of the lines of electric force. The equipotential lines have a direction which is perpendicular to the lines of electric force.

FIG. 1 illustrates the lines of electric force and the equipotential lines when a medium having uniform conductivity is present between the positive electrode and the negative electrode, and if an object having different conductivity is present as the medium, the lines of electric force and the equipotential lines are changed.

Figure 2:
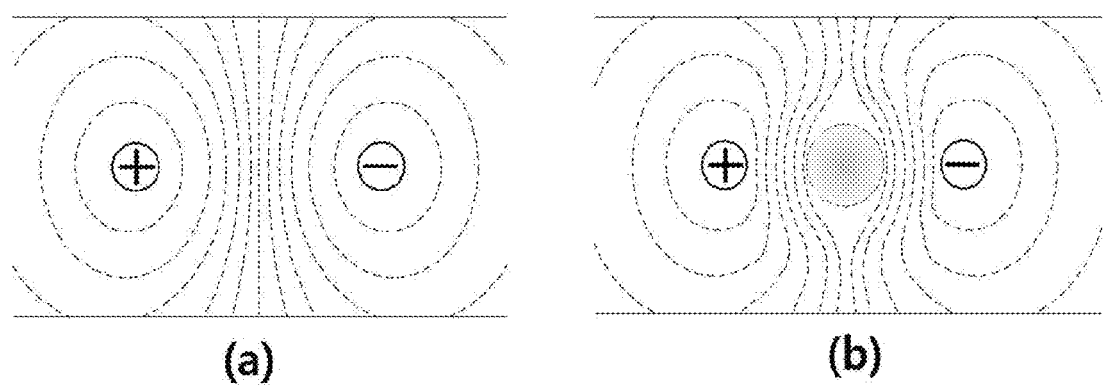
FIG. 2 is a diagram illustrating the equipotential lines changed in a case in which a conductor is present between the positive electrode and the negative electrode.

FIG. 2 is a diagram illustrating the equipotential lines changed in a case in which a conductor is present between the positive electrode and the negative electrode. (a) of FIG. 2 is a diagram illustrating the equipotential lines before the conductor is positioned between the positive electrode and the negative electrode. (b) of FIG. 2 is a diagram illustrating the equipotential lines after a circular conductor is positioned between the positive electrode and the negative electrode. As can be seen from FIG. 2, if the conductor is positioned between the positive electrode and the negative electrode, the equipotential lines (equipotential surface in 3D) are changed while an electric field is changed.

Therefore, by measuring a change in a voltage at several points between the positive electrode and the negative electrode, a presence of an object having different conductivity may be detected. The electric field is changed even in a case in which a detection target object has higher conductivity than the medium (water or seawater) as in FIG. 2, but since the electric field is changed even in a case in which the detection target object has lower conductivity than the medium, the presence of the detection target object may be detected.

For example, even in a case in which fresh water having conductivity different from that of seawater or a sea current having temperature different from that of seawater among properties of matter is flowing into the sea, since the electric field is changed due to different conductivity, the presence of the detection target objection may be detected.

Figure 3:
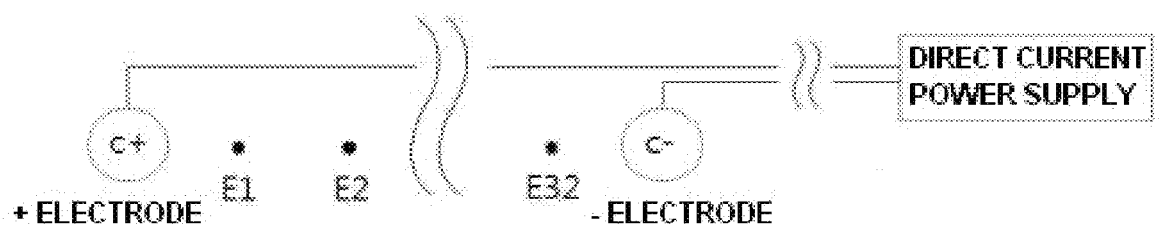
FIG. 3 is a diagram illustrating a plurality of measurement electrodes which are present between two direct current electrodes.

FIG. 3 is a diagram illustrating a plurality of measurement electrodes which are present between two direct current electrodes. In a case in which a direct current power supply supplies direct current power to two electrodes (C+ (positive electrode) and C− (negative electrode)) and voltages of 32 measurement electrodes (E1, E2, . . . , E32) are measured, the presence of the detection target object may be estimated. In this case, the two direct current electrodes and the measurement electrodes may be a graphite electrode, not a metal electrode. A voltage by which a current of tens of amperes flows may be applied between the two direct current electrodes, and a voltage having different magnitude may also be applied, if necessary.

Figure 4:
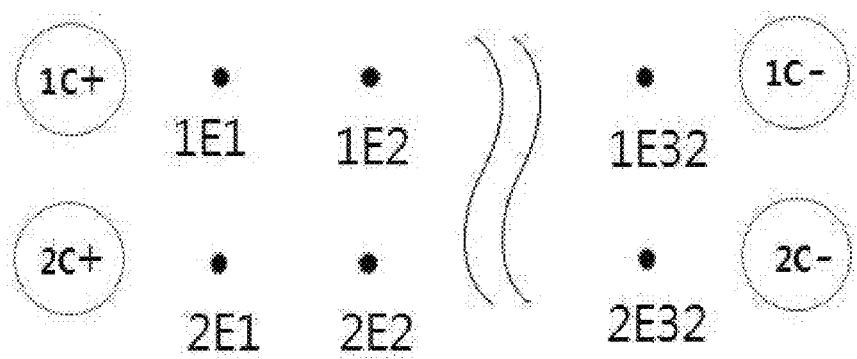
FIG. 4 is a diagram illustrating the direct current electrodes and the measurement electrodes which are disposed in two columns.

FIG. 4 is a diagram illustrating the direct current electrodes and the measurement electrodes which are disposed in two columns. In a case in which the plurality of measurement electrodes and the two direct current electrodes are disposed in one column as illustrated in FIG. 3, a movement direction and movement speed of the detection target object may not be estimated, but in a case in which the measurement electrodes are disposed in two columns as illustrated in FIG. 4, the movement direction and movement speed of the target object may also be estimated. If necessary, the direct current electrodes and the measurement electrodes may also be disposed in two or more columns.

Figure 5:
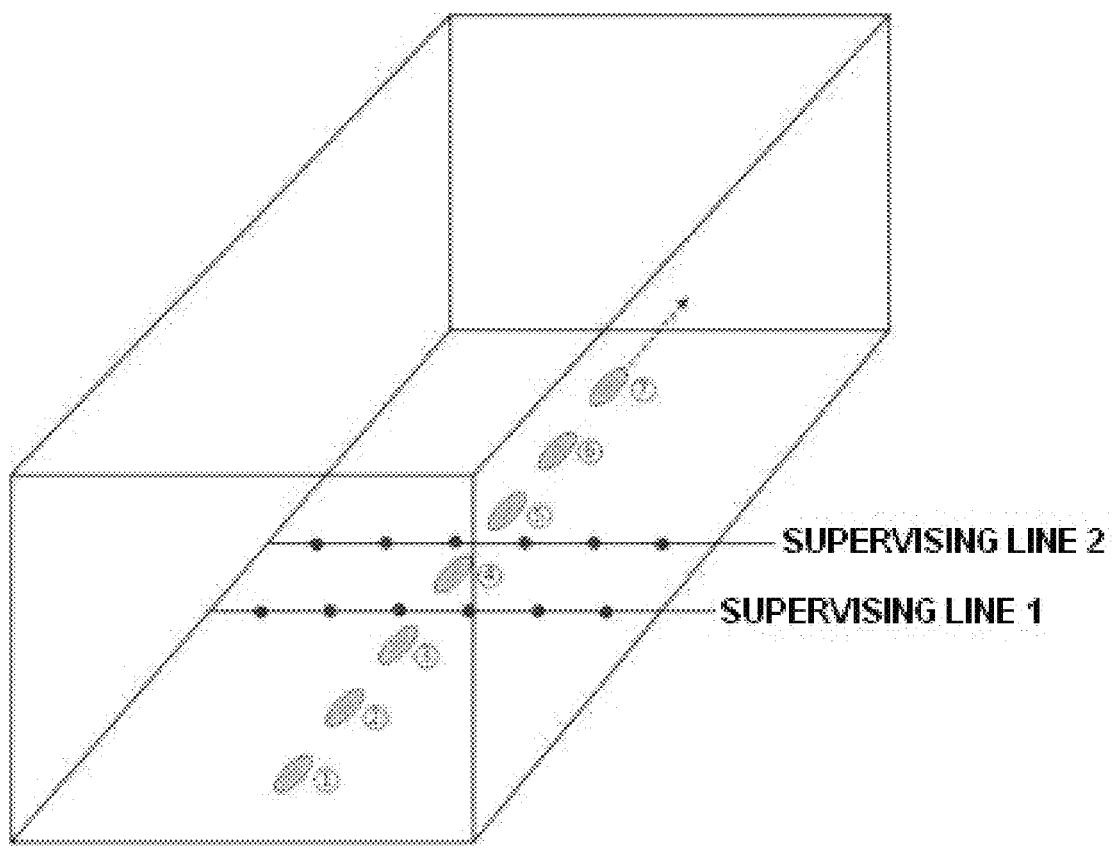
FIG. 5 is a diagram illustrating a moving body which is moved over the plurality of measurement electrodes.
Figure 6:
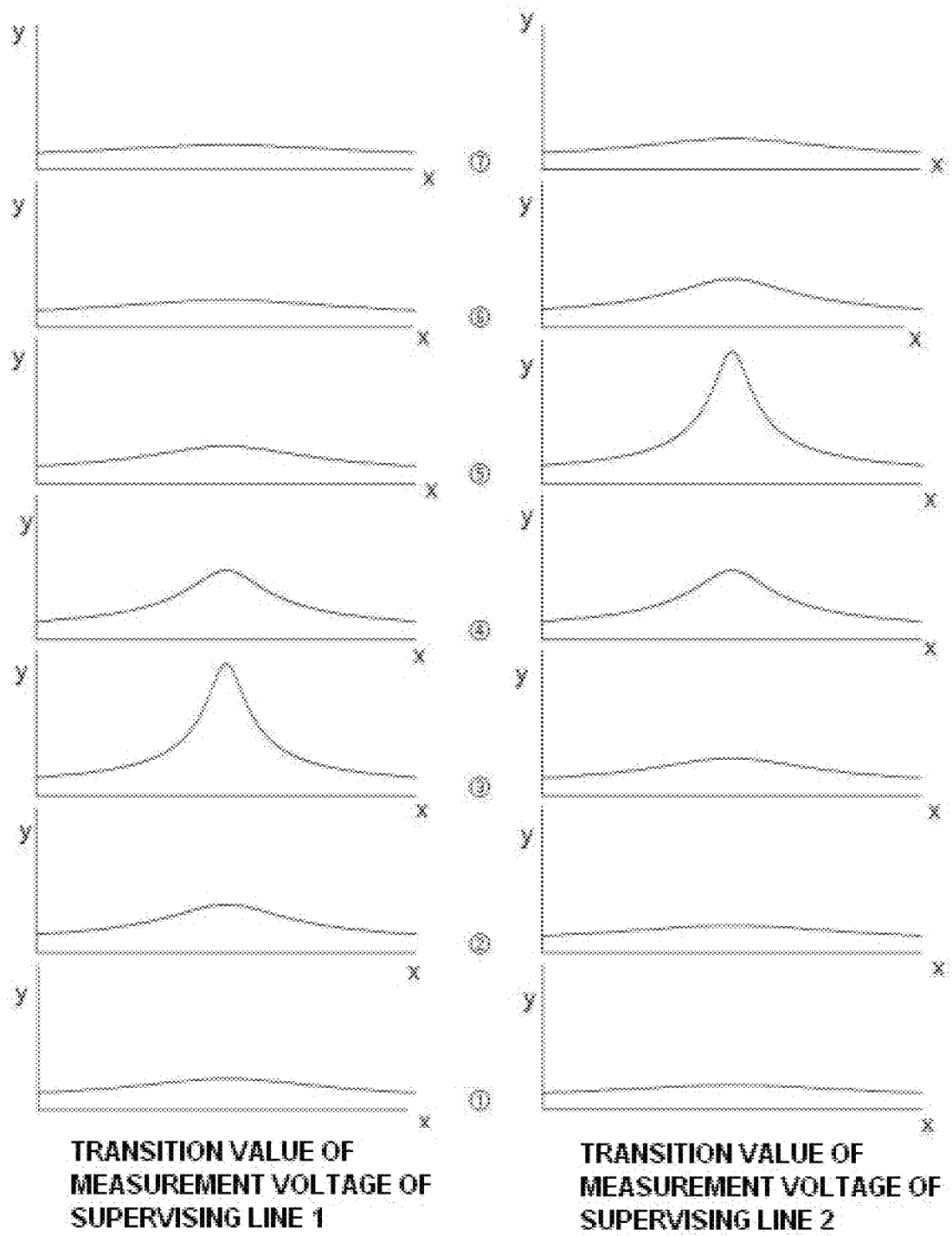
FIG. 6 is a graph of transition in a measurement value of the measurement electrode when the moving body is moved.

FIG. 5 is a diagram illustrating a moving body which is moved over the plurality of measurement electrodes and FIG. 6 is a graph of transition in a measurement value of the measurement electrode when the moving body is moved.

As illustrated in FIG. 5, if the moving body is sequentially moved from a location of no. 1 to a location of no. 7 in a situation in which the plurality of measurement electrodes are disposed in the two columns, a transition value (which is a difference between a voltage value when the target object is present and a voltage value when the target object is not present and may be indicated by an amount of potential change) of the voltage measured from the measurement electrodes is also changed along the movement of the moving body. It is likely that the transition value of the measurement value is high at the measurement electrode which is close to the moving body.

A left graph of FIG. 6 illustrates the transition value of the measurement voltage by the measurement electrode of a supervising line 1 and a right graph of FIG. 6 illustrates the transition value of the measurement voltage by the measurement electrode of a supervising line 2. An x axis of the left graph of FIG. 6 indicates locations of a plurality of electrodes of the supervising line 1 and an x axis of the right graph of FIG. 6 indicates locations of a plurality of electrodes of the supervising line 2.

It is seen from the graph that as the moving object is close to the measurement electrode, the transition value of the measurement voltage is increased, and as the moving object is far away from the measurement electrode, the transition value of the measurement voltage is decreased. In addition, it is likely that the measurement electrode from which the moving object proximately passes shows the largest voltage transition value.

In FIG. 6, since the transition values of the measurement voltages of the two columns are measured, the movement direction and movement speed of the moving object may also be estimated.

The direct current electrodes and the measurement electrodes may be installed to float underwater, but as illustrated in FIG. 5, if the direct current electrodes and the measurement electrodes are installed on a sea floor, there are advantages that the direct current electrodes and the measurement electrodes are easily fixed, and possibility that the direct current electrodes and the measurement electrodes are damaged by water or an underwater moving body is reduced.

Figure 7:
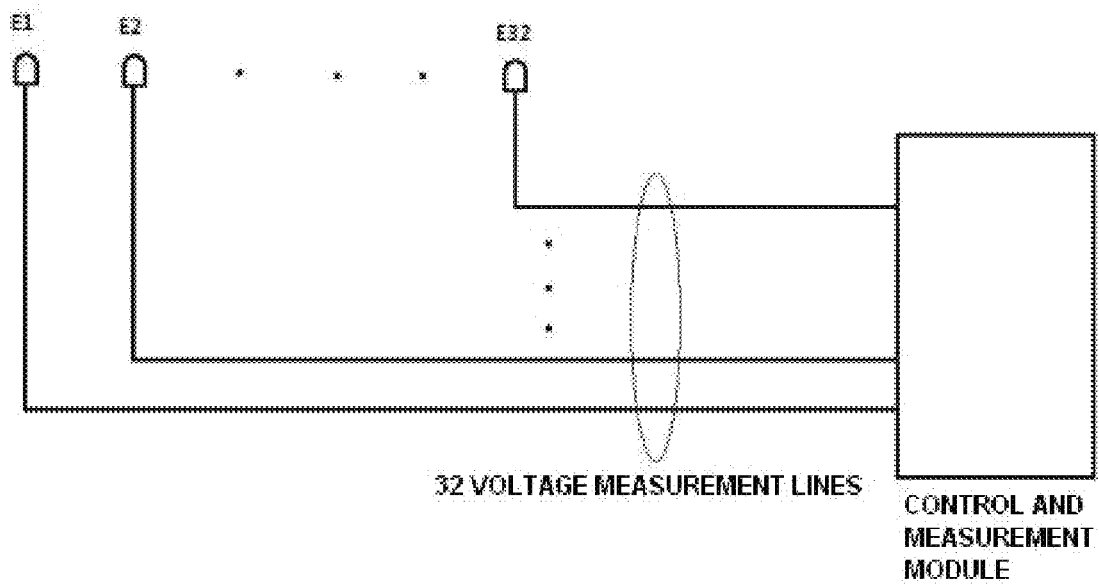
FIG. 7 is diagram illustrating connection lines connected to a control and measurement module and 32 measurement electrodes.

FIG. 7 is diagram illustrating connection lines (voltage measurement lines) connected to a control and measurement module and the 32 measurement electrodes. In measuring the voltages of the 32 measurement electrodes in the control and measurement module, the connection line may also be connected to each of the 32 measurement electrodes. However, in this case, there is a problem that a plurality of connection lines which are proportional to the number of measurement electrodes need to be connected to the control and measurement module.

In order to solve the above-mentioned problem, the number of connection lines (voltage measurement lines) may be reduced by installing an electrode control module including a switch and a controlling unit in each of the measurement electrodes.

Example 1

Figure 8:
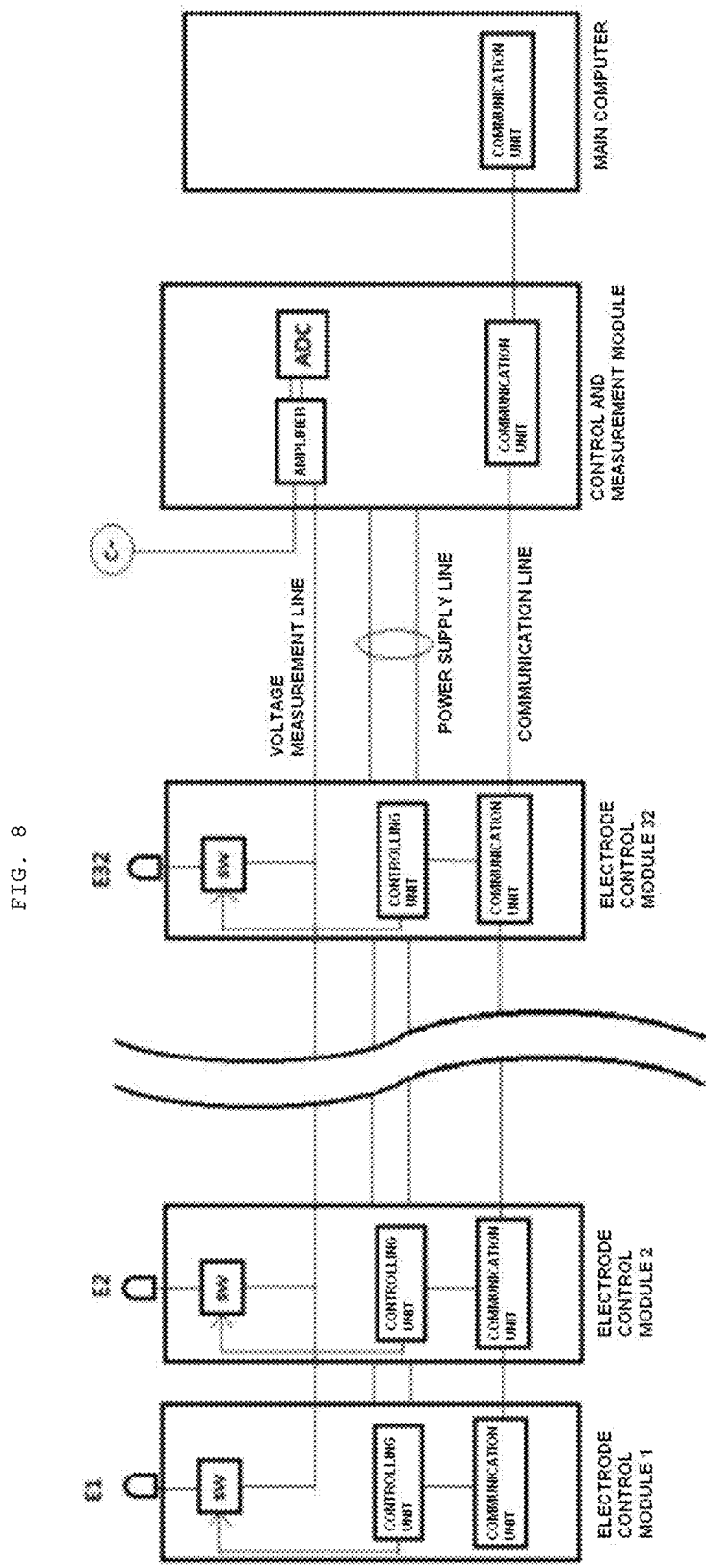
FIG. 8 is a conceptual diagram of a first example using an electrode control module.

FIG. 8 is a conceptual diagram of a first example using an electrode control module.

Only one voltage measurement line is present, and this voltage measurement line is connected to 32 electrode control modules. The 32 electrode control modules include a switch, a controlling unit, and a communication unit, respectively. A connection state between the measurement electrodes (E1 to E32) and the voltage measurement line is changed depending on a state of the switch. That is, if the switch is in a turn-on state, the voltage measurement line and the corresponding measurement electrode are connected, and if the switch is in a turn-off state, the voltage measurement line and the corresponding measurement electrode are not connected. The controlling unit controls the connection state of the switch. The communication unit enables communication between the control and measurement module and the 32 electrode control modules. An example of a device which may be used as the switch includes a small relay, an example of a device which may be used as the controlling unit includes a micro control unit (MCU), and an example of a device which may be used as the communication unit includes an RS-485 module. The control and measurement module instructs the controlling unit of each electrode control module to turn-on only the switch of the measurement electrode of which a voltage is to be measured, through communication and turn-off switches of the remaining measurement electrodes. In doing so, a voltage between the electrode C− and the measurement electrode may be measured. The control electrode module may amplify a signal (voltage) between the electrode C− and the measurement electrode using an amplifier, convert the amplified signal into a digital value using an analog-to-digital converter (ADC), and may then transmit the digital value to a main computer.

Example 2

Figure 9:
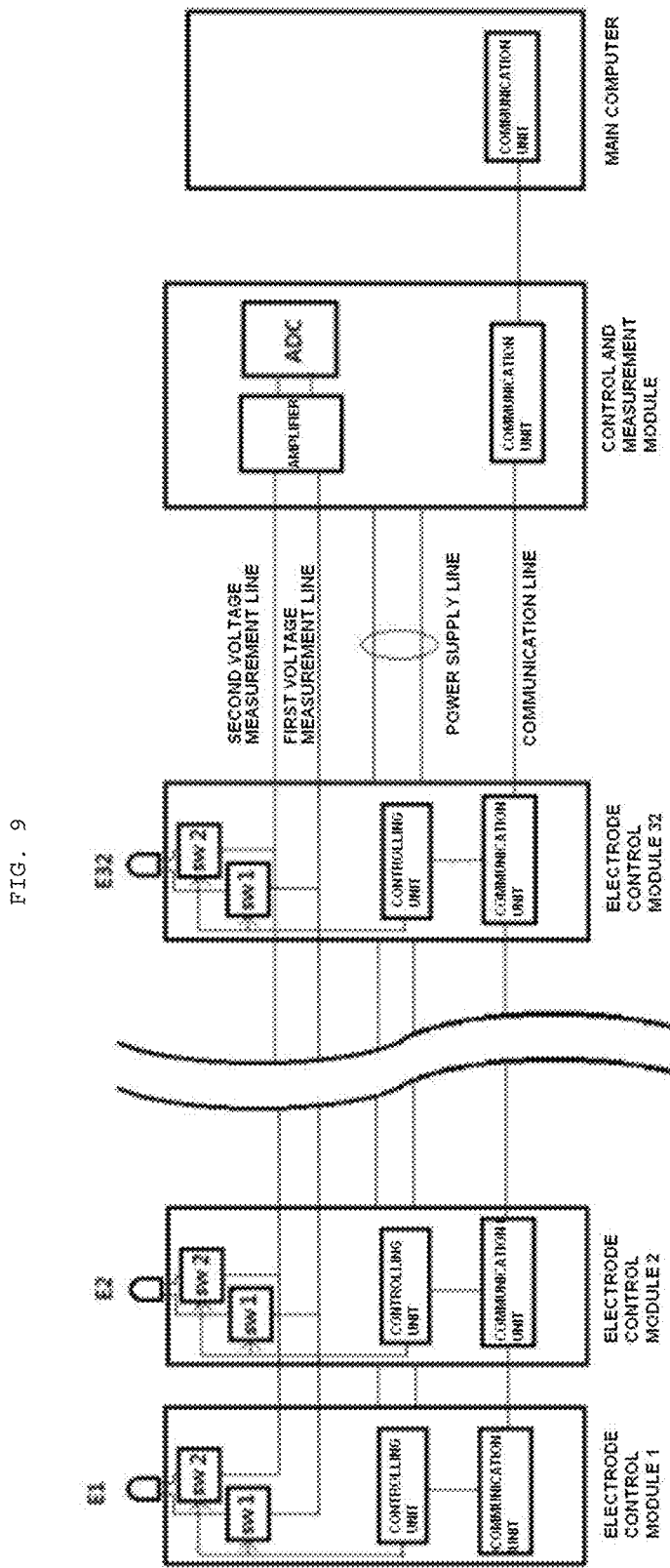
FIG. 9 is a conceptual diagram of a second example using an electrode control module.

FIG. 9 is a conceptual diagram of a second example using an electrode control module. A difference from the first example is that two voltage measurement lines (a first voltage measurement line and a second voltage measurement line) are present and two switches (a first switch SW1 and a second switch SW2) are provided to each of the electrode control module, such that the respective measurement electrodes may be selectively connected to the first switch SW1 or the second switch SW2. That is, a connection state between the measurement electrode and the first voltage measurement line is changed depending on a state of the first switch, a connection state between the measurement electrode and the second voltage measurement line is changed depending on a state of the second switch, and the controlling unit may control the states of the first switch and the second switch.

Therefore, any two measurement electrodes of the 32 measurement electrodes may be selected according to the control of the controlling unit and a voltage between the two selected measurement electrodes may be measured.

In this case, a differential voltage value between the respective measurement electrodes may also be sequentially calculated, but as a size of the target object is increased, a measurement result of an interval two times may also be obtained. That is, the voltage difference is measured by skipping one measurement electrode such as between E1 and E3, between E3 and E5, and between E5 and E7, not E1 and E2, between E2 and E3, and between E3 and E4, such that the detection target object having the size two times may be more efficiently detected. Here, it is also possible to perform a measurement of an interval three times and an interval four times as well as the interval two times.

Although the example 1 and the example 2 described above describe the case in which the number of measurement electrodes is 32, the number of measurement electrodes may be changed depending on design needs. In addition, a distance between the measurement electrodes may be 30 m, and may be appropriately changed depending on design needs.

In addition, there is no need to continuously connect the two direct current electrodes to the direct current power supply, and the two direct current electrodes may also be connected to the direct current power supply only at the necessary moment. In addition, a period at which the voltage of each measurement electrode is measured may also be changed depending on design needs.

The method as illustrated in FIG. 7 has an advantage that a multiplexing measurement may be rapidly performed without the electrode control module, but has a disadvantage that a thickness of a cable becomes thick and field installing costs and time are increased.

The methods described in the example 1 and the example 2 have a disadvantage in that a separate electrode control module is required, but have an advantage in that the number of voltage measurement lines is reduced to thereby reduce field installing costs and time.

The method described in the example 1 has a disadvantage in that the device is simpler than that of the example 2, but is vulnerable to noise. Since the example 2 requires the switches two times as many as the example 1, but measures only a voltage difference between the measurement electrodes which are adjacent to each other (differential mode), the example 2 has an advantage that the measurement may be more precisely performed.

The method for the underwater detection according to the present invention, which is a method for an underwater detection detecting an underwater moving object using an underwater detector including two direct current electrodes, a plurality of measurement electrodes, and a control and measurement module for measuring voltages of the plurality of measurement electrodes, includes the following operations.

First Operation: applying a direct current voltage to the two direct current electrodes;

Second Operation: periodically measuring the voltages of the plurality of measurement electrodes; and Third Operation: estimating the underwater moving object using the voltage measurement values.

When the underwater moving object is estimated using the voltage measurement values, it is preferable to estimate the underwater moving object using a difference value obtained by comparing the voltage measurement values with a normal state voltage, that is, a voltage transition value.

Contents of the estimation may include a presence, a size, movement speed, a movement direction, etc., of the underwater moving object.

The size of the underwater moving object may be estimated by the number of measurement electrodes having a large voltage transition value. It is likely that when the size of the underwater moving object is small, a strong measurement value transition occurs at one or two measurement electrodes, and it is likely that when the size of the underwater moving object is large, the strong measurement value transition occurs at a plurality of measurement electrodes.

According to the exemplary embodiment of the present invention, the underwater detector may accurately detect a presence of the moving object even in the region in which large noise occurs due to a strong tidal current, or a region in which the water layers having temperature and salinity differences are mixed. In addition, since an electrical method is used, the method for the underwater detection according to the present invention is a method in which the detection may be applied even under turbid water in which an optical visual identification is impossible. In addition, if conductivity is different from that of seawater, a nonconductor may be detected and a conductor (a kind of iron of a magnetic material as well as a nonferrous metal object of a nonmagnetic material) may also be detected.

What is claimed is:

1. An underwater detector comprising:
   two direct current electrodes installed underwater and connected to a direct current power supply;
   a plurality of measurement electrodes installed in a plurality of columns of two or more columns underwater; and
   a control and measurement module for measuring voltages of the plurality of measurement electrodes,
   wherein the plurality of measurement electrodes each include an electrode control module,
   the electrode control module includes a first switch, a second switch, a controlling unit, and a communication unit enabling communication with the control and measurement module,
   the electrode control module has a first voltage measurement line and a second voltage measurement line which are connected thereto,
   a connection state between the measurement electrodes and the first voltage measurement line is changed depending on a state of the first switch,
   a connection state between the measurement electrodes and the second voltage measurement line is changed depending on a state of the second switch,
   the controlling unit controls the states of the first switch and the second switch, and
   the voltages of the measurement electrodes are due to an electric field that occurs by a voltage of the direct current electrode.

2. The underwater detector of claim 1, wherein a direct current voltage is periodically applied to the two direct current electrodes.

3. The underwater detector of claim 1, wherein the direct current electrodes and the measurement electrodes are installed on a sea floor.

4. A method for an underwater detection detecting an underwater moving object using an underwater detector including two direct current electrodes installed underwater and connected to a direct current power supply, a plurality of measurement electrodes installed in a plurality of columns of two or more columns underwater, and a control and measurement module for measuring voltages of the plurality of measurement electrodes, the method comprising:
   applying a direct current voltage to the two direct current electrodes;
   periodically measuring the voltages of the plurality of measurement electrodes; and
   estimating the underwater moving object using voltage measurement values,
   wherein the voltages of the measurement electrodes are due to an electric field that occurs by a voltage of the direct current electrode,
   the plurality of measurement electrodes each include an electrode control module, and
   the electrode control module includes a first switch, a second switch, a controlling unit controlling states of the first switch and the second switch, and a communication unit enabling communication with the control and measurement module, such that if two measurement electrodes to be measured are selected when a voltage between the two measurement electrodes is measured, one measurement electrode of the two selected measurement electrodes is connected to the first switch and the other is connected to the second switch to thereby measure the voltage between the two measurement electrodes to be measured.

5. A method for an underwater detection detecting an underwater moving object using an underwater detector including two direct current electrodes installed underwater and connected to a direct current power supply, a plurality of measurement electrodes installed in a plurality of columns of two or more columns underwater, and a control and measurement module for measuring voltages of the plurality of measurement electrodes, the method comprising:
   applying a direct current voltage to the two direct current electrodes;
   periodically measuring the voltages of the plurality of measurement electrodes; and
   estimating the underwater moving object using a transition value of voltage measurement values,
   wherein the voltages of the measurement electrodes are due to an electric field that occurs by a voltage of the direct current electrode,
   the plurality of measurement electrodes each include an electrode control module, and
   the electrode control module includes a first switch, a second switch, a controlling unit controlling states of the first switch and the second switch, and a communication unit enabling communication with the control and measurement module, such that if two measurement electrodes to be measured are selected when a voltage between the two measurement electrodes is measured, one measurement electrode of the two selected measurement electrodes is connected to the first switch and the other is connected to the second switch to thereby measure the voltage between the two measurement electrodes to be measured.

* * * * *